United States Patent [19]

Sano et al.

[11] 4,110,467
[45] Aug. 29, 1978

[54] PROPHYLACTIC, THERAPEUTIC OR HYGIENICAL AGENT AGAINST VIRUS DISEASES IN FISH AND USE THEREFOR

[75] Inventors: Tokuo Sano, Numazu; Takeo Oshima, Habikino; Tokio Kamata, Hikone, all of Japan

[73] Assignee: Fujisawa Pharmaceutical Co., Ltd., Osaka, Japan

[21] Appl. No.: 751,327

[22] Filed: Dec. 13, 1976

[51] Int. Cl.$^2$ .................. A61K 31/335; A61K 33/34; A01K 61/00
[52] U.S. Cl. ................................ 424/280; 424/141; 424/143; 119/3
[58] Field of Search ............................... 424/280, 141

[56] References Cited

U.S. PATENT DOCUMENTS

| | | | |
|---|---|---|---|
| 2,907,658 | 10/1959 | Luther | 424/280 |
| 3,065,139 | 11/1962 | Ericsson et al. | 424/280 |
| 3,329,607 | 7/1967 | Colobert et al. | 424/280 |
| 3,681,492 | 8/1972 | Kotzbauer | 424/141 |

FOREIGN PATENT DOCUMENTS

| | | | |
|---|---|---|---|
| 2,041M | 9/1963 | France | 424/280 |
| 4,638,267 | 1/1970 | Japan | 424/180 |
| 760,659 | 11/1956 | United Kingdom | 424/280 |

*Primary Examiner*—Donald B. Moyer
*Attorney, Agent, or Firm*—Dayton R. Stemple, Jr.

[57] ABSTRACT

A prophylactic, therapeutic or hygienical agent effective for preventing or treating various virus diseases in fish, comprising at least one enediol compound or a salt thereof (e.g. ascorbic acid, erythorbic acid, or a salt thereof with an inorganic or organic base) in a combination with a heavy metal, preferably in the form of a water-soluble salt thereof (e.g. copper sulfate), and the use of the active agent for preventing or treating the virus diseases in fish by administering the active agent to the fish orally or parenterally or by bathing, washing or breeding the fish in an aqueous solution containing the active agent.

4 Claims, No Drawings

PROPHYLACTIC, THERAPEUTIC OR HYGIENICAL AGENT AGAINST VIRUS DISEASES IN FISH AND USE THEREFOR

The present invention relates to a composition for preventing or treating fish diseases caused by viruses and a method for preventing or treating the virus diseases of fish. More particularly, it relates to a prophylactic, therapeutic or hygienical agent against virus diseases of fish comprising as an essential active ingredient an enediol compound in a combination of a heavy metal, and the use of the enediol compound as the prophylactic, therapeutic or hygienical agent against virus diseases of fish.

Recently, the breeding of fish has been developing, but on the other hand, virus diseases have been prevalent and thereby many fishes to be bred, particularly fry of salmonids and eels, have died causing severe damage to the breeding of fish. There has unfortunately never been found any effective prophylactic, therapeutic or hygienical agent against the virus diseases in fish.

As the results of the present inventors' extensive studies, it has now been found that an enediol compound or a salt thereof can inactivate the viruses infectious to fish (e.g. salmonids and eels) and is useful for preventing or treating the virus diseases of fish. It has already been reported that some enediol compounds and a combination thereof with a heavy metal are effective against microorganisms, such as bacteria and viruses, infectious to human and animal body (cf. U.S. Pat. No. 3,065,139). However, that patent does not teach the use of the compounds for preventing and treating the virus diseases of fish. Moreover, the virus diseases of fish are far different from ones of human and animal body. For example, the virus diseases of fishes are transmitted through water, but in human and animal body, such diseases are transmitted through air or by contact with infected animals. So, in human and animal body, effective prophylactic or therapeutic means is almost limited through oral or intramuscular administration, but in fish bathing is more effective. This point is the most important difference in preventing or treating virus diseases between in fishes and in other animals.

An object of the present invention is to provide a prophylactic, therapeutic or hygienical composition against the virus diseases of fish.

Another object of the invention is to provide a method for preventing or treating the virus diseases of fish.

A further object of the invention is to provide a method for breeding effectively fish by preventing the infection of the fish with viruses.

These and other objects of the invention will be apparent from the following description.

The prophylactic, therapeutic or hygienical agent used in the present invention is an enediol compound, for instance, ascorbic acid, erythorbic acid (another name: isoascorbic acid), which also includes a salt thereof with an inorganic or organic base, such as sodium, potassium, ethanolamine, hexylamine, or the like. Further, the enediol compound is used in a combination with a heavy metal (e.g. copper), which gives better result. The heavy metal is usually used in the form of a water-soluble salt yielding the heavy metal ion, for instance, copper sulfate.

The prophylactic, therapeutic or hygienical agent used in the present invention is effective against various virus diseases in fish, for instance, Infectious Haematopoietic Necrosis (IHN), Viral Haemorrhagic Septicemia (VHS), Infectious Pancreatic Necrosis (IPN), Nerka Virus disease (NeVTA), or the like.

The term "fish" herein used has a very wide sense covering various non-mammarian aquatic animals which may be kept, raised or bred in fish culture industry, and representative examples of the fishes infectious with the above virus diseases are rainbow trout (*Salmo gairdnerii irideus*), red salmon (*Oncorhynchus nerka var. nerka*), silver salmon (*Oncorhynchus kisutch*), king salmon (*Oncorhynchus tschawytscha*), brown trout (*Salmo trutta fario*), land lock type red salmon (*Oncorhynchus nerka var. adonis*), dog salmon (*Oncorhynchus keta*), pink salmon (*Oncorhynchus gorbuscha*), and other Salmonid fishes, such as *Oncorhynchus masou*, *Oncorhynchus rhodurus*, *Salmo gairdnerii gairdnerii*, *Salmo salar*, *Salmo trutta*, eels (e.g. *Anguilla japonica*, *A. anguilla*, *A. rostrata*), catfish (e.g. *Ictalurus punctatus*), or the like.

The present prophylactic, therapeutic or hygienical agent may be applied to the fish in various modes as usually used for the prevention and treatment of virus fish diseases. Suitable mode may vary in accordance with the kinds of fish, the degree of growth, or the like. One of the typical modes is to administer the agent orally to fish in the form of a capsule or in an admixture with feed. Another typical mode is to treat temporarily fish with an aqueous solution of the agent by bathing or washing. A further typical mode is to breed fish in an appropriate medium (e.g. fresh water, brackish water, sea water) containing the agent. A still further typical mode is to inject the agent intraperitoneally or intramuscularly. Oral administration or injection may be performed to all ages of fish, and bathing or washing may be usually performed to fish egg or fry.

The amount of the agent to be applied may be variable with various factors, such as the species, size and age of fish, the kind of infection, the circumstances surrounding fish, the application mode and the like. When the enediol compound is applied without combination with the heavy metal, it is preferably used in an amount of 20 to 2,000, more preferably 200 to 2,000, mg/kg of fish per day in case of oral administration, and in case of administration in an admixture with feed, it is admixed with the feed in a ratio of 0.01 to 10% by weight, more preferably 0.1 to 10% by weight, on the basis of the whole weight of feed. In case of the application by bathing or washing, the compound is preferably used in a concentration of 20 to 10,000 ppm, more preferably 200 to 4,000 ppm. In case of breeding fish in an appropriate medium, the compound is preferably contained in a concentration of 20 to 10,000 ppm, more preferably 200 to 4,000 ppm, in the medium. Besides, in case of injection, the compound is preferably used in an amount of 50 to 500, more preferably 200 to 500, mg/kg of fish per day. These amount may be varied with the various factors as mentioned above and may be optionally decreased or increased.

When the enediol compound is used in a combination with the heavy metal, the amount of the enediol compound may be in the same ranges as mentioned above. The amount of the heavy metal is also variable with the various factors as mentioned above, but may be usually in a range of 0.0001 to 10 ppm, preferably 0.001 to 1 ppm as the heavy metal ion in case of bathing, washing or breeding, and 0.002 to 10 mg/kg of fish per day in case of oral administration or injection.

On application, the present prophylactic, therapeutic or hygienical agent may be used as it is, but it may be usually used in an admixture with various diluents for convenience in application, for instance, in the form of powders, particles, granules, tablets, capsules, solutions, emulsions, dispersions, or the like. The diluent may be solid or liquid diluents. Suitable examples of the diluents are water, ethanol, sucrose, feed oil, starch, talc, bentonite, fish meal, sodium carbonate, sodium hydrogen carbonate, or the like.

Other additives, such as nutrients, feeds, other antimicrobial agents, insecticides, metabolism modifiers, or the like may also be added to the composition.

The heavy metal and the endiol compound are contained in the present composition in the ratio of 1:500 to 1:10,000 (heavy metal: enediol compound).

Suitable examples of the preparation of the present invention are illustrated below, wherein "part" means part by weight.

| Preparation 1 | |
|---|---|
| Sodium erythorbate | 50 parts |
| Sucrose | 50 parts |
| Preparation 2 | |
| Ascorbic acid | 88 parts |
| Sodium hydrogen carbonate | 42 parts |
| Preparation 3 | |
| Sodium erythorbate | 100 parts |
| Malachite green | 0.15 part |
| Preparation 4 | |
| Sodium erythorbate | 100 parts |
| Methylene blue | 1 part |
| Preparation 5 | |
| Sodium erythorbate | 100 parts |
| Furazolidone | 0.5 part |
| Preparation 6 | |
| Sodium ascorbate | 100 parts |
| Tetracycline | 10 parts |

Particularly suitable examples of the preparation for oral administration are as follows.

Preparation 7

A mixture of erythorbic acid and oxytetracycline (1000:25 by weight) is admixed with feed for fish in an amount of 5% by weight based upon the whole weight of the mixture, and pellets are prepared from the mixture.

Separately, copper sulfate is admixed with feed for fish in an amount of 0.005% by weight based upon the whole weight of the mixture, and pellets are prepared from the mixture.

Both pellets thus prepared are mixed together in the ratio of 1:1 by weight to give a preparation suitable for oral administration.

Preparation 8

In the same manner as described in Preparation 7, pellets of a mixture of feed for fish and 5% by weight of erythorbic acid: beer yeast (1,000:25 by weight) and pellets of a mixture of feed for fish and copper sulfate (0.005% by weight) are prepared. Both pellets are mixed together in the ratio of 1:1 by weight to give a preparation.

Preparation 9

Erythorbic acid is suspended in water or feed oil (in an amount of 1/20–1/10 by weight of feed) so as to make a concentration of 2,000 mg/kg of fish, and the mixture is adsorbed into pellets of feed. Separately, copper sulfate is dissolved in water (1/20–1/10 by weight of feed) so as to make a concentration of 2 mg/kg of fish, and the solution is adsorbed into pellets of feed. Both pellets are mixed together in the ratio of 1:1 by weight to give a preparation.

| Preparation 10 | |
|---|---|
| Erythorbic acid | 500 mg |
| A mixture of copper sulfate and lactose (1 : 50 by weight) | 250 mg |

The above components are separately included in a capsule, and the capsule of erythorbic acid is orally administered and then the capsule of the mixture of copper sulfate and lactose is administered.

Examples of the preparation suitable for bathing are as follows.

Preparation 11

Erythorbic acid (2,000 mg) is added to water (10 liter) and thereto is added on aqueous solution of copper sulfate ($Cu^{++}$ content: 1 mg/ml, 2 ml).

Preparation 12

A mixture (400 mg) of erythorbic acid and lactose (1:1 by weight) is added to water (10 liter) and thereto is added an aqueous solution of copper sulfate ($Cu^{++}$ content: 1 mg/ml, 0.2 ml).

Preparation 13

A mixture (400 mg) of erythorbic acid and calcium carbonate (1:1 by weight) is added to water (10 liter) and therein is dissolved two tablets containing copper sulfate ($Cu^{++}$ content: 1 mg/tablet, base material: calcium carbonate).

Preparation 14

A mixture (4,000 mg) of erythorbic acid and sodium hydrogen carbonate (each equimolar amount of them is contained) is added to water (10 liter) and thereto is added an aqueous solution of copper sulfate ($Cu^{++}$ content: 1 mg/ml, 4 ml).

Preparation 15

A mixture (2,000 mg) of erythorbic acid and Malachite green (100:0.15 by weight) is added to water (10 liter) and thereto is added an aqueous solution of copper sulfate ($Cu^{++}$ content: 1 mg/ml, 2 ml).

Preparation 16

Erythorbic acid (2,000 mg) is added to water (10 liter) and therein is dissolved two tablets containing copper sulfate ($Cu^{++}$ content: 1 mg/tablet, base material: calcium carbonate).

The effects of the present prophylactic, therapeutic or hygienical agent against various viruses in fish in vitro or in vivo are illustrated by the following tests.

Test 1: Inactivation activity of the agent against virus in vitro

A mixture of 0.02 M tris(hydroxymethyl)aminomethane-hydrochloric acid (Tris) buffer (pH: 7.2, 9.8 ml) and an aqueous solution of copper sulfate (concentration: $10^{-5}$ M as copper, 0.1 ml) was added to four test tubes. To three test tubes among them was added each 0.1 ml of an aqueous solution of sodium ascorbate or sodium erythorbate having a concentration of 1, $10^{-1}$ or $10^{-2}$ mol/liter to give test preparations in ten times dilution series. As a Reference, to the remaining one test tube was added water (0.1 ml).

From each test tube, 4.5 ml of the preparation mentioned above was transferred to another test tube, and thereto was added an aqueous solution (0.5 ml) of IHN virus (viral titer: $10^{5.1}$ TCID$_{50}$/ml in case of I and $10^{6.1}$ TCID$_{50}$/ml in case of II). The mixture was stirred well with magnetic stirrer and was allowed to stand at 20° C. After 10, 30 and 60 minutes, a prescribed amount of the mixture was taken out from each test tube, from which test preparations were prepared by series (ten fold) dilution method. The test preparations (each 0.05 ml) were inoculated to RTG-2 cells (cells of the ovary of Salmo gairdnerii irideus) which have previously cultivated in the well on a micro plate until they grew up to 80% (became confluent). The mixture was cultivated at 15° C., on which the production of cell pathological effect (CPE) was observed through a microscope every day. After the cultivation for 14 days, the culture was fixed with formalin in a usual manner, dyed with 1% of crystal violet and then the final score of CPE was done. From the result, the viral titer was calculated, which is shown in the following Table 1.

Table 1

| Agent | Concentration of the agent (mol/liter) | Viral titer (TCID$_{50}$/ml) Time for contact of virus to the test preparation (minute) | | |
|---|---|---|---|---|
| | | 10 | 30 | 60 |
| Sodium erythorbate | $10^{-2}$ | 0 | 0 | 0 |
| | $10^{-3}$ | 0 | 0 | 0 |
| | $10^{-4}$ | 0 | 0 | 0 |
| Control | 0 | — | — | $10^{4.1}$ |
| Sodium ascorbate | $10^{-2}$ | — | — | 0 |
| | $10^{-3}$ | — | — | 0 |
| | $10^{-4}$ | — | — | $10^{4.3}$ |
| Control | 0 | — | — | $10^{5.1}$ |

[Remark]: The numeral "0" in the viral titer means that the virus was completely inactivated.
TCID means Tissue Culture Infectious Dose.

Test 2: Antiviral effect of the agent in fry of Salmo gairdnerii irideus

Material and Method

The test fish was fry of Salmo gairdnerii irideus weighing 0.2 g in average, which has been fed for 36 days.

To one liter beaker was added one liter of water containing IHN virus (viral titer: $10^{5.8}$ TCID$_{50}$/ml, 1 ml), and thereto was added sodium erythorbate in the final concentration of 2,000 ppm and further added copper sulfate in the final concentration of $10^{-7}$ M (as Cu$^{++}$). As a control, to another one liter beaker was added merely one liter of water containing IHN virus (viral titer: $10^{5.8}$ TCID$_{50}$/ml, 1 ml).

After aeration for one hour (liquid temperature: 10.4°–11.2° C.), 30 test fish were added to each of the beakers and were infected with the virus. Thereafter, the test fish were transferred from the beakers to water bathes wherein water was flowed at a rate of 2.1 liter/minute. The fish were thus kept in the water bath (liquid temperature: 8.0°–10.0° C.) and observed for 14 days during which they were fed one time per day.

Results

The dead number of the fish is shown in the following Table 2.

Table 2

| | Total dead number of fish | | | | | | | | | | |
|---|---|---|---|---|---|---|---|---|---|---|---|
| | 4 | 5 | 6 | 7 | 8 | 9 | 10 | 11 | 12 | 13 | 14$^{th}$ day |
| Treated with the agent | 0 | 1 | 1 | 2 | 2 | 2 | 2 | 2 | 2 | 2 | 2 |
| Control | 0 | 0 | 1 | 12 | 18 | 20 | 24 | 25 | 26 | 28 | 29 |

As is made clear from the above results, the erythorbic acid showed significant antiviral activity.

Test 3: Antiviral activity of the agent against IHN virus in vitro

An aqueous solution of IHN virus (viral titer: $10^{3.05}$ TCID$_{50}$/ml, 500 ml) was each added to four conical flasks, which were weakly aerated with a glass tube through the test.

To one flask was added sodium erythorbate in the final concentration of 2,000 ppm, and in another one flask was dissolved completely sodium erythorbate and thereto was added copper sulfate (CuSO$_4$.5H$_2$O) in the final concentration of 0.1 ppm (as Cu$^{++}$, 0.393 ppm as CuSO$_4$.5H$_2$O). The remaining two flasks were used as a control, to one of which was added only copper sulfate in a concentration of 0.1 ppm (as Cu$^{++}$) and another one of which was used as it is, i.e. without addition of any agent. These flasks were allowed to stand at 12° C. for 4 hours.

With respect to each solution of the flasks, it was checked whether the virus was still live or not by the following method.

At one hour after the preparation of the test solution and at the final time of the test (i.e. at 4 hour after the preparation of the test solution), a part of the solution (each 10 ml) of the flasks was taken out. 0.1 ml of the solution was inoculated to RTG-2 cells which were cultivated in a culture tube until they grew up to 80% (three culture tubes were used for each test solution) and the mixture was cultivated at 12° C. for two weeks, and then the production of CPE was observed through a microscope.

The results are shown in the following Table 3.

Table 3

| Contents of the test solution | Time for contacting the virus with the test solution | |
|---|---|---|
| | one hour | Four hours |
| Sodium erythorbate + CuSO$_4$.5H$_2$O | − − − | − − − |
| Sodium erythorbate | + + + | − − − |
| CuSO$_4$.5H$_2$O | + + + | + + + |
| No addition of the agent | + + + | + + + |

[Remark]: The symbols used in Table 3 have the following meaning.
+: CPE was produced (i.e. the virus lived)
−: No CPE was produced (i.e. the virus was dead)

Test 4: Antiviral activity of the agent against various viruses in fish

To a 0.02 M Tris buffer solution (pH: 7.2, 9.8 ml) was added 0.2 ml of a 10% aqueous solution of sodium erythorbate to prepare a solution of sodium erythorbate having a concentration of 2,000 ppm. To the solution (4.45 ml) was added an aqueous solution containing the test virus (0.5 ml) and thereto was further added aqueous solution of copper sulfate (0.05 ml) in the final concentration of $10^{-3}$ M (63.5 ppm as Cu$^{++}$), $10^{-5}$ M (0.635 ppm as Cu$^{++}$) or $10^{-7}$ M (0.00635 ppm as Cu$^{++}$) to prepare sodium erythorbate-virus-copper mixtures.

The test viruses were four sero-type viruses of IPN, i.e. BUHL strain (viral titer: $10^{7.55}$ TCID$_{50}$/ml), FR 10 strain (viral titer: $10^{7.8}$ TCID$_{50}$/ml), FR 21 strain (viral titer: $10^{7.8}$ TCID$_{50}$/ml) and VR 299 strain (viral titer: $10^{5.05}$ TCID$_{50}$/ml); three viruses isolated from viral and viral-like epizootics of eels, i.e. EVE (reovirus-like virus isolated from European eel, viral titer: $10^{8.05}$ TCID$_{50}$/ml), EVA (Rhabdovirus isolated from American eel, viral titer: $10^{5.3}$ TCID$_{50}$/ml) and EVX (Rhabdovirus isolated from French eel, viral titer: $10^{7.05}$ TCID$_{50}$/ml); and a virus isolated from viral epizootic of O. nerka, so-called NeVTA (Nerka Virus Towada Akita and Aomori, Herpesvirus-like virus, viral titer: $10^{3.8}$ TCID$_{50}$/ml).

The sodium erythorbate-virus-copper solution was stirred at 20° C. for 60 minutes with a magnetic stirrer, and thereafter, the sample solutions were taken out from each test solution and diluted with Hanks' BSS by series (ten fold) dilution method.

The test sample solutions (each 0.05 ml) thus prepared were each inoculated to RTG-2 cells which have previously cultivated in the well on a micro plate until they grew 80% (became confluent), and the resultant was incubated at 15° C. Every 24 hours during the incubation, the production of CPE was observed with a microscope. The viral titer (TCID$_{50}$/ml) was calculated on the basis of production of CPE at 14th day of the cultivation.

The results are shown in the following Table 4.

Table 4

| Kind of virus | Viral titer (TCID$_{50}$/ml) | | | Control (not treated with the agent) |
|---|---|---|---|---|
| | Treated with the agent Sodium erythorbate: 2,000 ppm Conc. of copper sulfate as Cu$^{++}$ | | | |
| | $10^{-3}$M | $10^{-5}$M | $10^{-7}$M | |
| IPN virus | | | | |
| BUHL strain | 0 | $10^{2.05}$ | — | $10^{7.55}$ |
| FR 10 strain | 0 | 0 | — | $10^{7.8}$ |
| FR 21 strain | 0 | 0 | — | $10^{7.8}$ |
| VR 299 strain | 0 | 0 | — | $10^{5.05}$ |
| Virus isolated from eel | | | | |
| EVE | — | 0 | $10^{6.55}$ | $10^{8.05}$ |
| EVA | — | 0 | $10^{4.8}$ | $10^{5.3}$ |
| EVX | — | 0 | $10^{5.8}$ | $10^{7.05}$ |
| NeVTA virus | 0 | 0 | — | $10^{3.8}$ |

[Remark]: In the table, "0" means no production of CPE, and "—" means that it was not tested.

What is claimed is:

1. A method for preventing virus disease selected from the group consisting of Infectious Haematopoietic Necrosis, Viral haemorrhagic Septicemia, Infectious Pancreatic Necrosis, Nerka virus disease and viral epizootics in fish selected from the group consisting of Salmonid and eels, which comprises bathing said fish in 20 to 10,000 ppm aqueous solution of erythorbic acid or its sodium salt and a water-soluble salt yielding 0.0001 to 10 ppm Cu$^{++}$ in said solution.

2. The method according to claim 1, wherein the concentration of erythorbic acid or its salt is 200 to 4,000 ppm.

3. The method according to claim 1, wherein the concentration of said Cu$^{++}$ is 0.001 to 1 ppm.

4. The method according to claim 1, wherein said salt is copper sulfate.

* * * * *